United States Patent [19]

Berg et al.

[11] Patent Number: 4,897,161

[45] Date of Patent: Jan. 30, 1990

[54] SEPARATION OF VINYL ACETATE FROM ETHYL ACETATE BY EXTRACTIVE DISTILLATION

[75] Inventors: Lloyd Berg, 1314 S. 3rd Ave., Bozeman, Mont. 59715; Marc W. Paffhausen, Bozeman, Mont.

[73] Assignee: Lloyd Berg, Bozeman, Mont.

[21] Appl. No.: 326,086

[22] Filed: Mar. 20, 1989

[51] Int. Cl.$^4$ .......................... B01D 3/40; C07C 67/54
[52] U.S. Cl. .......................................... 203/51; 203/56; 203/59; 203/63; 203/64; 203/DIG. 10; 560/248
[58] Field of Search ................... 560/248; 203/56, 51, 203/59, 63, 64, DIG. 10

[56] References Cited

U.S. PATENT DOCUMENTS

| | | | |
|---|---|---|---|
| 3,458,406 | 7/1969 | Fisher et al. | 203/DIG. 10 |
| 3,591,463 | 7/1971 | Copelin | 203/61 |
| 3,691,021 | 9/1972 | Feldman et al. | 560/248 |
| 3,736,236 | 5/1973 | DiFiore et al. | 203/64 |
| 3,905,875 | 9/1975 | Kronig et al. | 560/248 |

*Primary Examiner*—Wilbur Bascomb

[57] ABSTRACT

Vinyl acetate cannot be easily removed from ethyl acetate by distillation because of the closeness of their boiling points. Vinyl acetate can be readily separated from ethyl acetate by means of extractive distillation using certain glycols or glycol ethers. Typical effective agents are 2-methyl-2,4-pentanediol, 1,3-butanediol, ethylene glycol methyl ether and diethylene glycol ethyl ether.

6 Claims, No Drawings

SEPARATION OF VINYL ACETATE FROM ETHYL ACETATE BY EXTRACTIVE DISTILLATION

This invention relates to a method for separating vinyl acetate from ethyl acetate using certain glycols or glycol ethers as the agents in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Vinyl acetate and ethyl acetate boil only four Celcius degrees apart and thus have a relative volatility of only 1.08. Table 1 shows the relationship between relative volatility and plate requirements for rectification. With its relative volatility of only 1.08, the separation of vinyl acetate from ethyl acetate in 99% purity requires 160 plates of 75% efficiency. If a method could be found to increase the relative volatility to 1.28, the plate requirement would be only 49. Extractive distillation would be an attractive method of effecting the separation of vinyl acetate from ethyl acetate if agents can be found that (1) increase the relative volatility of vinyl acetate to ethyl acetate and (2) are easy to recover from ethyl acetate, that is, form no azeotrope with ethyl acetate and boil sufficiently above ethyl acetate to make separation possible with only a few theoretical plates.

TABLE 1

| Rectification Column Plates Required for 99% Separation | |
|---|---|
| Relative Volatility | Plates, 75% Efficiency |
| 1.08 | 160 |
| 1.15 | 88 |
| 1.20 | 67 |
| 1.23 | 60 |
| 1.28 | 49 |

Extractive distillation typically requires the addition of an equal amount to twice as much extractive agent as vinyl acetate-ethyl acetate on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with ethyl acetate, other wise it will form a two-phase azeotrope with the ethyl acetate in the recovery column and some other method of separation will have to be employed.

OBJECTIVE OF THE INVENTION

The object of this invention is to provide a process or method of extractive distillation that will enhance the relative volatility of vinyl acetate from ethyl acetate in their separation in a rectification column. It is a further object of this invention to identify organic compounds which are stable, can be separated from ethyl acetate by rectification with relatively few plates and can be recycled to the exractive distillation column and reused with little decomposition.

SUMMARY OF THE INVENTION

The objects of the invention are provided by a process for separating vinyl acetate from ethyl acetate which entails the use of certain glycols or glycol ethers, either alone or admixed, as the agent in extractive distillation.

TABLE 2

| Effective Extractive Distillation Agents | | |
|---|---|---|
|  | Ratio | Relative Volatility |
| 2-Methyl-2,4-pentanediol | 2 | 1.25 |
| 2-Methyl-2,4-pentanediol, Ethylene glycol methyl ether | 1:1 | 1.28 |
| 2-Methyl-2,4-pentanediol, Diethylene glycol ethyl ether | 1:1 | 1.20 |
| 2-Methyl-2,4-pentanediol, Butoxypropanol | 1:1 | 1.15 |
| 1,3-Butanediol | 2 | 1.19 |
| 1,3-Butanediol, Ethylene glycol methyl ether | 1:1 | 1.23 |
| Butoxypropanol | 2 | 1.17 |
| Ethylene glycol methyl ether | 2 | 1.20 |
| Diethylene glycol ethyl ether | 2 | 1.19 |
| Ethylene glycol methyl ether, Diethanol amine | 1:1 | 1.22 |

TABLE 3

Data From Runs Made In Rectification Column

| Agent | Column | Time, hrs. | Weight % Vinyl Acetate | Weight % Ethyl Acetate | Relative Volatility |
|---|---|---|---|---|---|
| 2-Methyl-2,4-pentanediol-Ethylene gylcol methyl ether | Overhead Bottoms | 0.5 | 66 45.3 | 34 54.7 | 1.173 |
| 2-Methyl-2,4-pentanediol-Ethylene glycol methyl ether | Overhead Bottoms | 1 | 66.4 46 | 33.6 54 | 1.180 |
| 2-Methyl-2,4-pentanediol-Ethylene glycol methyl ether | Overhead Bottoms | 1.5 | 65.4 40.5 | 34.6 59.5 | 1.213 |
| 1,3-Butanediol-Ethylene glycol methyl ether | Overhead Bottoms | 0.5 | 68.4 43.8 | 31.6 56.2 | 1.212 |
| 1,3-Butanediol-Ethylene glycol methyl ether | Overhead Bottoms | 1 | 66 44.6 | 34 55.4 | 1.180 |

DETAILED DESCRIPTION OF THE INVENTION

We have discovered that certain glycols and glycol ethers, either alone or in mixtures will effectively increase the relative volatility of vinyl acetate to ethyl acetate and permit the separation of vinyl acetate from ethyl acetate by rectification when employed as the agent in extractive distillation. Table 2 lists the glycol ethers and their mixtures and the approximate proportions that we have found to be effective. The data in Table 2 was obtained in a vapor-liquid equilibrium still. In each case, the starting material was a 50—50% weight percent mixture of vinyl acetate and ethyl acetate. The ratios are the parts by weight of extractive agent used per part of vinyl acetate-ethyl acetate mixture. The compounds which

TABLE 4

| Potential Extractive Distillation Agents Which Are Ineffective |
|---|
| 1,4-Butanediol |
| 1,5-Pentanediol |
| 1,6-Hexanediol |
| Diethylene glycol |
| Dipropylene glycol |
| Ethylene glycol ethyl ether |
| Ethylene glycol hexyl ether |
| Ethylene glycol phenyl ether |
| Ethylene glycol diacetate |
| Diethylene glycol methyl ether |
| Propylene glycol methyl ether |
| Propylene glycol propyl ether |
| Propylene glycol isobutyl ether |
| Dipropylene glycol methyl ether |
| Glycerol triacetate |
| Triethylene glycol |
| Tripropylene glycol methyl ether |
| 1,3-Butanediol - Diethylene glycol ethyl ether |
| 1,4-Butanediol - Diethylene glycol methyl ether |
| 1,4-Butanediol - Diethylene glycol diethyl ether |
| Ethylene glycol methyl ether - Triethylene glycol |
| Ethylene glycol methyl ether - Dimethyl isopropanol amine |
| Diethylene glycol ethyl ether - Diethyl ethanol amine | are effective when used alone are 2-methyl-2,4-pentanediol, 1,3-butanediol, butoxypropanol, ethylene glycol methyl ether and diethylene glycol ethyl ether. The compound which is effective when used in a mixture is diethanolamine.

The relative volatilities shown in Table 2 were determined in a vapor-liquid equilibrium still. For example, in Table 2, one part of 2-methyl-2,4-pentanediol mixed with one part of the vinyl acetate-ethyl acetate mixture gives a relative volatility of 1.25. One half part of 1,3-butanediol mixed with one half part of ethylene glycol methyl ether with one part of the vinyl acetate-ethyl acetate mixture gives a relative volatility of 1.28. In every example in Table 2, the starting material is a vinyl acetate-ethyl acetate mixture which possesses a relative volatility of 1.08.

Two of the mixtures, 2-methyl-2,4-pentanediol-ethylene glycol methyl ether and 1,3-butanediol-ethylene glycol methyl ether, listed in Table 2 and whose relative volatility had been determined in the vapor-liquid equilibrium still, were then evaluated in a glass perforated plate rectification column possessing 5.3 theoretical plates and the results listed in Table 3. After one hour of continuous operation with 2-methyl-2,4-pentanediol-ethylene glycol methyl ether, the overhead was 66.4% vinyl acetate, 33.6% ethyl acetate, the bottoms was 46% vinyl acetate, 54% ethyl acetate which is a relative volatility of 1.18. After a half hour of continuous operation with 1,3-butanediol-ethylene glycol methyl ether, the overhead was 68.4% vinyl acetate, 31.6% ethyl acetate, the bottoms was 43.% vinyl acetate, 56.2% ethyl acetate which is a relative volatility of 1.21.

Table 4 lists several extractive distillation agents which might have been expected to be effective but which produced a relative volatility too low to be attractive.

THE USEFULNESS OF THE INVENTION

The usefulness or utility of this invention can be demonstrated by referring to the data presented in Tables 1, 2 and 3. All of the successful extractive distillation agents show that vinyl acetate and ethyl acetate can be separated from their mixtures by means of distillation in a rectification column and that the ease of separation as measured by relative volatility is considerable. Without these extractive distillation agents, little improvement will occur in the rectification column. The data also show that the most attractive agents will operate at a boilup rate low enough to make this a useful and efficient method of recovering high purity vinyl acetate from any mixture with ethyl acetate. The stability of the compounds used and the boiling point difference is such that complete recovery and recycle is obtainable by a simple distillation and the amount required for makeup is small.

WORKING EXAMPLES

Example 1

Fifty grams of a vinyl acetate-ethyl acetate mixture and 50 grams of 2-methyl-2,4-pentanediol were charged to a vapor-liquid equilibrium still and refluxed for twelve hours. Analysis indicated a vapor composition of 51.7% vinyl acetate, 48.3% ethyl acetate, a liquid composition of 46.2% vinyl acetate, 53.8% ethyl acetate which is a relative volatility of 1.25.

Example 2

Fifty grams of a vinyl acetate-ethyl acetate mixture, 25 grams of 1,3-butanediol and 25 grams of ethylene glycol methyl ether were changed to the vapor-liquid equilibrium still and refluxed for five hours. Analysis indicated a vapor composition of 53.7% vinyl acetate 46.3% ethyl acetate, a liquid composition of 48.5% vinyl acetate, 51.5% ethyl acetate which is a relative volatility of 1.23.

Example 3

A glass perforated plate rectification column was calibrated with ethylbenzene and p-xylene which possesses a relative volatility of 1.06 and found to have 5.3 theoretical plates. A solution comprising 100 grams of vinyl acetate and 100 grams of ethyl acetate was placed in the stillpot and heated. When refluxing began, an extractive agent comprising 50% 2-methyl-2,4-pentanediol and 50% ethylene glycol methyl ether was pumped into the column at a rate of 20 ml/min. The temperature of the extractive agent as it entered the column was 85° C. After establishing the feed rate of the extractive agent, the heat input to the vinyl acetate and ethyl acetate in the stillpot was adjusted to give a total reflux rate of 10-20 ml/min. After one hour of operation, the overhead and bottoms samples of approximately two ml. were collected and analysed by gas chromatography. The overhead analysis was 66.4% vinyl acetate, 33.6% ethyl acetate. The bottoms analysis was 46% vinyl acetate, 54% ethyl acetate. Using these compositions in the Fenske equation, with the number of theoretical plates in the column being 5.3, gave an average relative volatility of 1.18 for each theoretical plate. After one and one half hours of total operating time, the overhead and bottoms samples were again taken and analysed. The overhead composition was 65.4% vinyl acetate, 34.6% ethyl acetate and the bottoms composition was 40.5% vinyl acetate, 59.5% ethyl acetate. This gave a relative volatility of 1.213.

Example 4

One hundred grams each of vinyl acetate and ethyl acetate was placed in the stillpot of the column used in Example 3. An extractive agent comprising 50% 1,3-butanediol and 50% ethylene glycol methyl ether was pumped in. After one half hour of operation, the overhead analysis was 68.4% vinyl acetate, 31.6% ethyl acetate, the bottoms analysis was 43.8% vinyl acetate, 56.2% ethyl acetate which is a relative volatility of 1.212. After one hour of continuous operation, the overhead analysis was 66% vinyl acetate, 34% ethyl acetate, the bottoms analysis was 44.6% vinyl acetate, 55.4% ethyl acetate which is a relative volatility of 1.18. These data are presented in Table 3.

We claim:

1. A method for recovering vinyl acetate from mixtures of vinyl acetate and ethyl acetate which comprises distilling a mixture of vinyl acetate and ethyl acetate in a rectification column in the presence of about one part of an extractive agent per part of vinyl acetate-ethyl acetate mixture, recovering vinyl acetate as overhead product and obtaining the ethyl acetate and the extractive agent from the stillpot, in which the extractive agent comprises diethylene glycol ethyl ether.

2. A method for recovering vinyl acetate from mixtures of vinyl acetate and ethyl acetate which comprises distilling a mixture of vinyl acetate and ethyl acetate in a rectification column in the presence of about one part of an extractive agent per part of vinyl acetate-ethyl acetatc mixture, recovering vinyl acetate as overhead product and obtaining the ethyl acetate and the extractive agent from the stillpot, in which the extractive agent comprises butoxypropanol.

3. A method for recovering vinyl acetate from mixtures of vinyl acetate and ethyl acetate which comprises distilling a mixture of vinyl acetate and ethyl acetate in a rectification column in the presence of about one part of an extractive agent per part of vinyl acetate-ethyl acetate mixture, recoverinng vinyl acetate as overhead product and obtaining the ethyl acetate and the extractive agent from the stillpot, in which the extractive agent comprises 2-methyl 2,4-pentanediol and one material selected from the group consisting of ethylene glycol methyl ether, diethylene glycol ethyl ether and butoxypropanol.

4. A method for recovering vinyl acetate from mixtures of vinyl acetate and ethyl acetate which comprises distilling a mixture of vinyl acetate and ethyl acetate in a rectification column in the presence of about one part of an extractive agent per part of vinyl acetate-ethyl acetate mixture, recovering vinyl acetate as overhead product and obtaining the ethyl acetate and the extractive agent from the stillpot, in which the extractive agent comprises ethylene glycol methyl ether and 1,3-butanediol.

5. A method for recovering vinyl acetate from mixtures of vinyl acetate and ethyl acetate which comprises distilling a mixture of vinyl acetate and ethyl acetate in a rectification column in the presence of about one part of an extractive agent per part of vinyl acetate-ethyl acetate mixture, recovering vinyl acetate as overhead product and obtaining the ethyl acetate and the extractive agent from the stillpot, in which the extractive agent comprises butoxypropanol and 1,3-butanediol.

6. A method for recovering vinyl acetate from mixtures of vinyl acetate and ethyl acetate which comprises distilling a mixture of vinyl acetate and ethyl acetate in a rectification column in the presence of about one part of an extractive agent per part of vinyl acetate-ethyl acetate mixture, recovering vinyl acetate as overhead product and obtaining the ethyl acetate and the extractive agent from the stillpot, in which the extractive agent comprises ethylene glycol methyl ether and diethanolamine.

* * * * *